United States Patent [19]

Moorer et al.

[11] 3,986,979

[45] Oct. 19, 1976

[54] PROCESS FOR MAKING COMBINATION WETTING-DISPERSING AGENT

[75] Inventors: Howard H. Moorer, Charleston; Charles W. Sandefur, Charleston Heights, both of S.C.

[73] Assignee: Westvaco Corporation, New York, N.Y.

[22] Filed: Sept. 23, 1971

[21] Appl. No.: 183,261

Related U.S. Application Data

[63] Continuation-in-part of Ser. No. 825,051, May 15, 1969, abandoned.

[52] U.S. Cl. .................................... 252/353; 71/3; 252/352; 252/354; 252/355; 424/286; 424/315; 424/353; 424/354
[51] Int. Cl.² .................. B01F 17/02; B01F 17/12; B01F 17/26
[58] Field of Search ........... 252/352, 353, 354, 355; 424/315; 106/308 S

[56] References Cited
UNITED STATES PATENTS

| | | | |
|---|---|---|---|
| 2,298,650 | 10/1942 | Samaras et al. | 252/559 |
| 2,491,832 | 12/1949 | Savesen et al. | 252/353 X |
| 2,933,452 | 4/1960 | Byrd | 252/353 |
| 3,154,466 | 10/1964 | Nothum | 252/353 X |
| 3,342,581 | 9/1967 | Woodward et al. | 252/353 X |

*Primary Examiner*—Richard D. Lovering
*Attorney, Agent, or Firm*—Richard L. Schmalz; Ernest B. Lipscomb, III

[57] ABSTRACT

A process for making a wetting-dispersing agent whereby an aqueous mixture of a sulfonated lignin dispersing agent and an anionic or nonionic wetting agent in a weight ratio of dispersing agent to wetting agent of from about 19:1 to 1:3 are dried together to form a single product for use as a surfactant in pesticide formulations.

2 Claims, No Drawings

3,986,979

PROCESS FOR MAKING COMBINATION WETTING-DISPERSING AGENT

CROSS REFERENCE TO RELATED APPLICATION

This application is a continuation-in-part of our co-pending application, Ser. No. 825,051, filed May 15, 1969, and now abandoned.

BACKGROUND OF THE INVENTION

This invention relates to a process for the manufacture of a single wetting-dispersing agent for use in the manufacture of wettable powder formulations. More particularly, this invention relates to a process of making an improved combination wetting-dispersing agent for use in the formulations of insecticides, herbicides and fungicides.

For many years, manufacturers of pesticide toxicants have incorporated surfactants into formulations to make the active ingredient readily dispersable and wettable. Development of satisfactory surfactants has encountered various undesirable characteristics relating to suspendibility, aging, ease of formulation and foaming. The development of satisfactory surfactants is further hampered by the competitive nature of the industry, thereby causing the formulator to cut costs to a bare minimum. This means the use of the largest amount of diluent possible and the cheapest surfactants possible.

Until this invention, manufacturers of pesticide formulations were forced to separately mix into the wettable powder formulation both the wetting agent and the dispersing agent. Heretofore such conventional mixing means as a ball mill, a hammer mill, ribbon blender or the like, were necessarily used because of deficiencies in either the wetting agent or the dispersing agent or both, due to such adverse properties as physical form.

As noted above, it is well known to add separately a wetting agent and a dispersing agent to pesticide formulations. Examples of this practice are described in U.S. Pat. Nos. 2,893,912 and 3,342,581. The advantages of the instant invention over these patents lies in the ability of the manufacturer of pesticide formulations to utilize a substantially smaller total quantity of surfactant due to the synergistic effect obtained upon drying. The provision of a single surfactant for pesticide formulations replaces the need for separate wetters and dispersants, reduces inventory and storage problems, decreases the possiblity of error in preparing formulations and reduces the need for mixing and handling.

It is a general object of this invention to provide a surfactant for use in pesticide formulations which combines both wetting and dispersing functions in a single powdered product. It is another object of this invention to provide a process for making a single surfactant by drying together a wetting agent and a dispersing agent. It is a further object of this invention to provide a single wetting-dispersing agent which easily combines in a pesticide formulation by simple dry blending. It is still a further object of this invention to provide pesticide formulations having a single wetting-dispersing agent combined therein and characterized by outstanding suspendibility and aging properties. Other objects will be evident from the following disclosure.

SUMMARY OF THE INVENTION

It has been found that a single surfactant combining both wetting and dispersing functions may be made by drying together certain aqueous mixtures of wetting agents and dispersing agents to form a dry, powdered product providing significant advantages over conventional wetting and dispersing agents added individually to pesticide formulations. The single wetting-dispersing surfactant of this invention comprises from 5 to 75 percent by weight of a wetting agent dried together with 95 to 25 percent by weight of the dispersing agent. Of the various drying means used to obtain the single product of this invention, spray drying is preferred.

DETAILED DESCRIPTION OF THE INVENTION

The Dispersing Agents

The dispersing agents employed by this invention are the water-soluble sulfonated lignins.

In general, the sulfonated lignins used in this invention may come from any source. One of the main sources of lignins is the paper and pulp industry where lignocellulosic materials such as wood, straw, corn stalks, bagasse, and the like are processed to separate the cellulose or pulp from the lignin. When lignin is obtained from the kraft or sulfate pulping processes, it must be sulfonated before use as a dispersing agent. For example, the lignin products obtained in an alkaline or neutral process of digestion of lignocellulosic materials may be readily sulfonated by reacting with a bisulfite or sulfite. In other pulping processes, such as the sulfite process, lignin is made soluble by sulfonation and thus separated from the cellulose by dissolving in the spent liquor and is present in this liquor as a lignosulfonate. Any of the above-described sulfonated lignin materials may be used to produce the dispersing agent of the present invention. The degree of refining to which these sulfonated lignin materials are subjected, will depend on the quality of product desired and upon the economic factors involved. That is, refining to some extent will improve the properties of the final processed product, but the degree of improvement will not always be economically justifiable.

Although sulfonated lignins from all sources are contemplated, the sulfonated lignins made from alkali lignin are preferred. A particular class of dispersing agents preferred in this invention are the alkali metal salts of alkali lignin, particularly sodium sulfonated lignin. Although sodium sulfonated lignin is preferred, chemically modified sulfonated lignins may be used. These lignins are commercially available at varying solids contents. The solids concentration of the sulfonated lignin before adding to the aqueous solution of wetting agent is not critical.

The Wetting Agents

The wetting agents contemplated by this invention include both nonionic and anionic wetting agents. The cationic wetting agents are not feasible because of their incompatibility with the sulfonated lignin dispersing agents. In choosing a particular wetting agent it should be remembered that in the art of formulating a particular pesticide, that specific wetting agents should be considered for the particular toxicant under consideration.

The anionic wetting agents of this invention include such classes as sulfated fatty alcohols, sulfated olefins, sulfated amide condensates, alkyl-aryl polyether sulfates, alkyl sulfonates, sulfonated amides, sulfonated ethers and alkyl-aryl sulfonates. Of the anionic type wetting agents the sulfonated amides are particularly satsifactory.

The sulfonated amides especially contemplated are the type formed by condensing the acid halide of a fatty acid (such as oleoyl chloride) with an amine (such as methyl taurine). These amides are prepared from surface-active substances including, without limitation, decanoic, lauric, octanoic, tridecanoic, myristic, palmitic, arachidic, behenic, carnaubic, stearic, pentadecanoic, oleic, myristoleic and palmitoleic acids, and mixtures of acids, such as, coconut oil acid, peanut oil acid, safflower oil acid, linseed oil acid, and especially tall oil acids. Specific examples of suitable surface-active substances include, the lauric acid ester of sodium isethionate, the palmitic acid ester of potassium isethionate, the n-tridecanoic acid ester of sodium isethionate, the myristic acid ester of sodium isethionate, the stearic acid ester of sodium isethionate, the myristoleic acid ester of sodium isethionate, the coconut oil acid and oleic acid esters of sodium isethionate, sodium N-cyclohexyl-N-palmitoyl-taurate, sodium N-methyl-oleoyltaurate, sodium N-coconut acid-N-methyl-taurate, potassium N-propyl-N-myristoyl-taurate, sodium N-methyl-N-tallow acid taurate, sodium N-methyl-N-tall oil acid-taurate, and sodium N-hexyl-N-palmitoyl-taurate. Wetting agents of the type described above are sold commercially under the trade names Igepon A and Igepon T.

The nonionic wetting agents of this invention include fatty acid-alkanolamine condensates, ethylene oxide adducts of fatty acids, ethylene oxide adducts of fatty alcohols, alkyl-aryl polyether alcohols and polypropylene glycol-ethylene oxide condensates. Of the nonionic wetting agents the alkyl-aryl polyether alcohols are especially successful.

The alkyl-aryl polyether alcohols especially contemplated are alkyl phenols condensed with 9 to 12 moles of ethylene oxide to form an adduct. Specific examples include the ethylene oxide adducts of nonyl phenol, octyl phenol, lauryl phenol and polypropylene glycol.

The Single Surfactant

The single powdered product from one each of the above-named wetting agents and dispersing agents is formed by mixing the agents in solution together and drying in order to obtain the desired advantages. The ratio by weight of dispersing agent to wetting agent may be from 19:1 to 1:3 or in other words 25 to 95% by weight dispersing agent and 5 to 75 percent by weight wetting agent. The ratio of dispersant to wetting agent is entirely dependent upon the particular pesticide toxicant contemplated. Drying the wetting agent-dispersing agent mixture greatly improves the performance of wettable powders and produces dramatic efficiencies in formulation. Any number of conventional drying methods may be used. For instance, spray drying, force air drying, oven drying, drum drying, and freeze drying, with spray drying being preferred. As stated, spray drying is preferred and the parameters necessary are well known to those skilled in the art; however, particularly successful products may be spray dried at air inlet temperatures of from 200° to 900° F. and outlet air temperatures of between 155° and 400° F. The aqueous mixture of wetting and dispersing agent is normally diluted to an easily handled viscosity prior to spray drying, i.e., 30–45% solids content.

In fact, using the single surfactant of this invention formulators may make a saving of up to 25% of the total surfactants previously used, and normally savings are over 10%. Besides easier handling, the use of a single, dual-action product results in a more uniform distribution of the surfactant on wettable powder. This better distribution consequently leads to less product use, that is, less than the total wetting agent plus dispersing agent previously needed to produce the same result. Because one product may now be used instead of two products, formulation error and inventory problems decrease significantly.

A further and highly significant advantage is that the single product of this invention possesses aging properties superior to the wetting agents or dispersing agents and used either alone or mixed together. The aging properties of the single surfactant are especially improved when the wetting agent is a fatty acid-sulfonated amide. This is believed due to the antioxidant properties of the sulfonated lignin.

In addition to a wetting agent and a dispersing agent, the single powdered surfactant of this invention may include up to 30% of the total weight of the single surfactant of a builder. Builders are added to aid in preventing precipitation, especially where the aqueous mixture is formed with hard water. Examples of typical builders include the polyphosphates and silicates. More specifically sodium hexametaphosphate, tetrapotassium pyrophosphate, tetrasodium pyrophosphate, sodium tripolyphosphate and sodium silicate. Other examples of builders include nitrilotriacetic acid.

The single surfactant of this invention is added to pesticide formulations in amounts of 0.5% up to 10% of the total pesticide formulation, but preferably not over 4% by weight.

The Pesticide Formulations

The single surfactants of this invention have been incorporated into pesticide wettable-powder formulations to specifically show their advantage over conventional pesticide formulations. The pesticide powders of this invention include compounds active as insecticides, nematocides, fungicides, miticides and herbicides. The primary powder ingredient in pesticide formulations is the toxicant referred to hereafter as the "active ingredient". Typical formulations of conventionally milled wettable powders may vary as follows:

| COMPONENTS | PERCENT BY WEIGHT, % |
| --- | --- |
| Active Ingredient | 5–98 |
| Diluent | 0–92 |
| Dispersing Agent | .5–6 |
| Wetting Agent | .5–6 |

The active ingredients contemplated for utilization with the single surfactant of the present invention are any water-insoluble or very slightly water-soluble compounds conventionally employed or adapted to be employed in the preparation of wettable powder formulations. Specific examples, such as, D.D.T. (dichlorodiphenyltrichloroethane), Lindane (gamma-benzene hexachloride), Maneb (manganese ethylene bisdithiocarbamate), zinc ethylene bisdithiocarbamate, Aldrin (HHDN) (1,2,3,4,10, 10-hexachloro-1,4,4a,5,8,8a- hexahydro-1,4,5,8-endo, exodimethanonaphthalene), Dieldrin (the 6,7-epoxy derivative of Aldrin), Endrin (the endoexo isomer of dieldrin), Captan (N-(trichloromethyl )thio)-4-cyclohexene-1,2-dicarboximide), Malathion (S-[1,2-bis(ethoxycarbonyl)ethyl-]O,O-dimethyl phosphorodithioate), Parathion (O,O-diethyl-O-para-nitrophenyl phosphorothioate), cuprous oxide, copper oxychloride, copper arsenate, N,N'-dimethylurea, maleic hydrazide, sulfur and benzene hexachloride. The above list is shown by way of example and is not intended to limit the active ingredients useable in this invention.

A substantial portion of the water-insoluble powder ingredient of the wettable powder formulations of the invention may be present as an inert filler or carrier, called a diluent. The amount of diluent in a specific embodiment of the formulations of this invention, depends, inter alia, on the nature of the active ingredient and contemplated use of the wettable powder formulation. Specific examples of diluents includes clays, such as Barden clay, bentonite, and kaolinite. Other diluents include diatomaceous earth, calcium limes, calcites, dolomites, gypsum mica, talc, silicas, pyprophyllites, phosphates, calcium carbonate and barium sulfate.

It should be pointed out that particular wetting agents perform better with specific active ingredients. For example, the insecticide D.D.T. performs better with an anionic wetting agent of the sulfonated amide type than with other wetting agents. However, this is also the case when using separately added wetting and dispersing agent.

The Testing Procedures

The suspensibility test is run by weighing 3.33 grams of powder into a 100 ml. beaker. Next, add 50 ml. of distilled water and allow to stand for 30 seconds. Stir the mixture by hand for 30 seconds, then transfer to a 100 ml. graduated cylinder. Add sufficient water to make 100 ml. of suspension. Stopper the cylinder and invert smoothly, on a fixed imaginary axis, 30 times at the rate of one inverting and righting cycle every 2 seconds. Immerse the cylinder in a 30° C. constant temperature bath and allow to stand for 30 minutes. Next, remove the stopper and pipet a 25 ml. aliquot from the 50 ml. mark of the graduate. Transfer the aliquot to an evaporating dish and dry in a forced air oven at 100° C. Add approximately 15 ml. benzene to the dried sample and allow to stand 10 minutes to aid in extraction. Prepare a filter by loosely packing the stem of a filter tube with benzene-washed cotton. Wet the cotton well and filter the sample into a tared 50 ml. beaker. Add a fresh 15 ml. portion of benzene to the evaporating dish and scrub the bottom and sides well. After the first extract has filtered into the beaker, pour the second portion through the filter tube; after this has filtered rinse the tube with about 5 ml. of benzene. Evaporate the benzene in a 60° C. water bath using a gentle current of dry air. After the volume of benzene solution has evaporated to about 10 ml., add approximately 3 ml. isopropanol (C.P.) and continue evaporating to about 5 ml. of solution; add a second 3 ml. of isopropanol and evaporate to dryness. Transfer the beaker to a forced air oven at 65° C. and dry for 20 minutes. Weight the residue.

The accelerated aging test is run by weighing 5 g. of powder into a 25 × 200 mm. test tube. If the height of the powder in the tube exceeds 6.0 cm., compact the powder by gently tapping the tube until the level is reduced to 6.0 cm. Immerse the tube to a depth of at least 9.0 cm. in an oil bath maintained at 70° ± 0.1° C. The bath should be equipped with an electric stirrer, and the tubes must not be stoppered. Allow the sample to remain in the bath for two hours, then remove and cool to room temperature. Mix the sample well and test as in the normal suspensibility test, using 342 ppm. hard water.

The suspensibility percentage is determined by drying at 100° C. a 25 cc aliquot withdrawn from the midpoint of a 100 cc sample prepared by (1) adding 2.00 grams wettable powder to 50 ml. of 342 ppm. hard water and allowing it to stand +sec., (2) stirring for 30 sec. and diluting to the mark in a 100 ml. graduate, (3) inverting and righting the graduate 30 times over 60 seconds and (4) allowing the graduate to stand undisturbed for 30 minutes at 30° C. The suspensibility percent is calculated:

$$\frac{(\text{weight solids in aliquot}) \times 4 \times 100}{\text{weight original sample}}$$

The practice of the invention may clearly be seen in the following examples.

EXAMPLE 1

A single surfactant was prepared by mixing an aqueous solution of sodium N-methyl-N-tall oil-taurine with sodium sulfonated lignin at a weight ratio of 1:1 and thoroughly stirred. The aqueous mixture at a solids content of about 40% by weight was spray dried at an inlet air contact temperature of 550° F. to yield the single surfactant. Typical properties of this product were:

| | |
|---|---|
| Solids, % | 97.4 |
| Ash, % | 19.0 |
| pH | 8.8 |
| Insolubles, % | 0.08 |

To evaluate the properties of the single surfactant of this invention the one-shot surfactant above was substituted for the wetting agent and the dispersing agent of the following D. D. T. wettable-powder formulation referred to as the "control" formulation:

| Ingredient | Percent by Weight |
|---|---|
| D.D.T. (Technical Grade) | 75.8 |
| Solid Diluent[1] | 20.2 |
| Dispersing Agent[2] | 2.0 |
| Wetting Agent[3] | 2.0 |

Notes:
[1]a hydrated amorphous silica.
[2]sodium sulfonated lignin.
[3]sodium-N-methyl-N-oleoyl-taurate.

The control formulation (4% wetting agent and dispersing agent) was compared to a 3.5% addition of the single surfactant. The results are shown in the table below.

| Test | Control Formulation | 3.5 % single Surfactant |
|---|---|---|
| Initial Suspensibility | 2.53 | 2.49 |
| Suspensibility after standard accelerated aging test | 2.50 | 2.53 |
| Suspensibility after compaction | | |

-continued

| Test | Control Formulation | 3.5 % single Surfactant |
| --- | --- | --- |
| to 1 g/2cc wgt. to volume ratio and accelerated aging test | 1.70 | 2.26 |
| Wetting time, sec. | 28 | 26 |

The results show that when using 12½% less of the single surfactant of this invention than the separate wetting agent and dispersing agent of the control formulation, that initial suspensibility and wetting time are approximately the same. Besides the outstanding saving in amount of material used, the single surfactant retains much of its suspensibility after aging, 2.26 as compared to 1.70.

EXAMPLE 2

A single surfactant especially useful in fungicide formulations was made by spray drying at a 1:1 ratio a mixture of sodium sulfonated lignin and sodium N-methyl-N-oleoyl-taurate. This surfactant was formulated into the following fungicide formulation in place of separately added wetting agents and dispersing agent.

| Ingredient | Formulation A %, by weight | Formulation B %, by weight |
| --- | --- | --- |
| Maneb (Technical Grade) | 94.1 | 94.1 |
| Solid Diluent[1] | 1.9 | 1.9 |
| Dispersing Agent[2] | 2.0 | |
| Anionic Wetting Agent[3] | 2.0 | |
| Single Surfactant | | 4.0 |

Notes:
[1]amorphous silica, Hi-Sil 233.
[2]sodium sulfonated lignin (Polyfon H).
[3]sodium-N-methyl-N-oleoyl-taurate.

The formulations were compared to each other for suspensibility and wetting time. Formulation B, using the single surfactant of this invention, had a suspensibility of 93.6% as compared to only 82.6% for Formulation A. The wetting time for Formulation B was 50 seconds compared to 120 + seconds for Formulation A.

EXAMPLE 3

A single surfactant especially useful in insecticide formulations was made by spray drying together a 3:1 weight ratio of sodium sulfonated lignin and a nonionic wetting agent, the ethylene oxide adduct of nonyl phenol. This single surfactant was made into the following insecticide formulation:

| Ingredient | Control %, by weight | Single Surfactant %, by weight |
| --- | --- | --- |
| Benzene Hexachloride[1] | 67 | 67 |
| Diluent[2] | 27 | 28 |
| Dispersing Agent[3] | 5 | |
| Wetting Agent[4] | 1 | |
| Single Surfactant | | 5 |

Notes:
[1]BHC (14 % gamma isomer) at 57 %
BHC (40 % gamma isomer) at 10 %
[2]barium sulfate.
[3]sodium lignosulfonate (Marasperse N).
[4]modified alkyl-napthylene sodium sulfonate (Petro WP).

These formulations were compared for suspendibility and wetting time. The formulation employing the single surfactant had a suspendibility of 52.3%; whereas the control formulation had a suspendibility of only 18.9%. The wetting time for both the control formulation and the single surfactant formulation was satisfactory.

EXAMPLE 4

An insecticide formulation was made to determine the effects on suspensibility upon aging of a single surfactant. The single surfactant of Example 2 was formulated with D.D.T. by air milling together 3.5 gms. of single surfactant with 76.8 gms. of D.D.T. (Technical Grade) and 19.7 gms. of a solid diluent, HiSil. The suspendibility was determined by both compacted aging and natural aging.

| Time | Suspensibility |
| --- | --- |
| Initial | 2.59 |
| Standard accelerated aging | 2.53 |
| Compacted aging[1] | 2.18 |
| 1 month[2] | 1.98 |
| 3 months[2] | 1.80 |
| 6 months[2] | 1.55 |
| 12 months[2] | 1.67 |

Notes:
[1]suspensibility after compaction to 1 gm/2cc. and accelerated aging test.
[2]suspensibility after compaction to 1 gm/cc and chronological aging.

The results show that in every instance the suspensibility of the aged single surfactant remained well above the minimum suspensibility of 1.25 required by U.S. Government specification AID-W.H.O. 2373-5.

EXAMPLE 5

A single surfactant was prepared by mixing an aqueous solution of sodium N-methyl-N-tall oil-taurine with sodium sulfonated lignin at a weight ratio of 1:1 and thoroughly stirred. The aqueous mixture at a solids content of about 40% by weight solids was divided into three equal portions. The portions were dried by oven drying, spray drying and freeze drying.

To evaluate the properties of each surfactant, each was substituted for the wetting agent and dispersing agent of the control formulation of Example 2, except the level of addition was 3.5%. The results are shown in the table below.

| Test | Spray Drying | Forced Air Oven Drying | Freeze Drying |
| --- | --- | --- | --- |
| Initial Suspensibility | 2.41 | 2.53 | 2.46 |
| Wetting time, sec. | 40 | 24 | 30 |

The results show that equally advantageous results are obtained regardless of the manner of drying.

While the invention has been described and illustrated herein by references to various specific materials, procedures and examples, it is understood that the invention is not restricted to the particular materials, combinations of materials, and procedures selected for that purpose. Numerous variations of such details can be employed, as will be appreciated by those skilled in the art.

What is claimed is:

1. A process for making a single wetting-dispersing agent which comprises, spray drying together a mixture of from 25 to 95 percent by weight of a sulfonated lignin dispersing agent and 75 to 5 percent by weight of an anionic wetting agent from the group consisting of sulfated fatty alcohols, sulfated olefins, sulfated amide condensates, alkyl-aryl polyether sulfates, alkyl sulfonates, sulfonated amides, sulfonated ethers and alkyl-aryl sulfonates.

2. A process for making a single wetting-dispersing agent which comprises, spray drying together a mixture of from 25 to 95 percent by weight of a sulfonated lignin dispersing agent and 75 to 5 percent by weight of a nonionic wetting agent from the group consisting of fatty acid-alkanolamine condensates, ethylene oxide adducts of fatty acids, ethylene oxide adducts of fatty alcohols, alkyl-aryl polyether alcohols and polypropylene glycolethylene oxide condensates.

* * * * *